United States Patent
Eskelinen

(10) Patent No.: US 6,990,174 B2
(45) Date of Patent: Jan. 24, 2006

(54) METHOD AND APPARATUS FOR PERFORMING SINGLE-POINT PROJECTION IMAGING

(75) Inventor: Jaakko Joonas Eskelinen, Helsinki (FI)

(73) Assignee: Instrumentarium Corp., Tuusula (FI)

(*) Notice: Subject to any disclaimer, the term of this patent is extended or adjusted under 35 U.S.C. 154(b) by 93 days.

(21) Appl. No.: 10/736,447

(22) Filed: Dec. 15, 2003

(65) Prior Publication Data

US 2005/0129173 A1 Jun. 16, 2005

(51) Int. Cl.
 *A61B 6/14* (2006.01)

(52) U.S. Cl. .............................. 378/38; 378/39; 378/40
(58) Field of Classification Search ................ 378/38, 378/39, 40, 195, 156, 197, 205, 207
See application file for complete search history.

(56) References Cited

U.S. PATENT DOCUMENTS

| | | | | |
|---|---|---|---|---|
| 4,783,793 A | * | 11/1988 | Virta et al. .................... | 378/39 |
| 5,784,429 A | * | 7/1998 | Arai .............................. | 378/38 |
| 6,256,369 B1 | | 7/2001 | Lai | |
| 6,452,997 B1 | * | 9/2002 | Muller et al. .................. | 378/17 |
| 6,470,069 B1 | * | 10/2002 | Muller ......................... | 378/21 |
| 6,731,717 B2 | * | 5/2004 | Kopsala ....................... | 378/38 |

* cited by examiner

*Primary Examiner*—Craig E. Church
*Assistant Examiner*—Irakli Kiknadze
(74) *Attorney, Agent, or Firm*—Andrus, Sceales, Starke & Sawall, LLP

(57) ABSTRACT

A method and apparatus for performing single-point projection imaging uses an X-ray source and a line scan camera present at a set distance therefrom and provided with a digital detector. The X-ray source, as well as the line scan camera, are adapted to rotate around an object placed between the X-ray source and the line scan camera. The X-ray source's focal spot is aligned at a desired position and the object is then imaged by scanning it with a beam emanating from the X-ray source, which beam is received by the detector of the line scan camera. The scanning motion is effected in such a way that the focal spot remains essentially stationary during the imaging process.

5 Claims, 2 Drawing Sheets

METHOD AND APPARATUS FOR PERFORMING SINGLE-POINT PROJECTION IMAGING

BACKGROUND OF THE INVENTION

The present invention relates to a method for performing single-point projection imaging by using an X-ray apparatus, comprising an X-ray source and a line scan camera present at a set distance therefrom and provided with a digital detector, the X-ray source as well as the line scan camera being adapted to rotate around an object to be placed between the X-ray source and the line scan camera.

Traditionally, such single-point projection imaging operations have been performed, as illustrated schematically in FIG. 1, by using an area detector 4 and a point-like focus 1, from which emanates an X-ray beam through an object 2 for a projection 3 on the detector. This type of single-point projection imaging produces a projection image, in which an object becomes recorded over its entire depth on a detector.

SUMMARY OF THE INVENTION

It is an object of the present invention to provide a solution, which enables this type of single-point projection imaging to be performed by using a small area detector to avoid the use of a large and expensive area detector. Another object is to provide a solution, which enables single-point projection imaging to be performed from a wide range of directions with a single apparatus without a necessity of realigning the object between separate imaging procedures. Yet another object is to provide a solution, which is implementable even with presently available X-ray equipment provided only with necessary reprogramming.

In view of fulfilling these objects, the inventive method comprises performing the alignment of the focal spot of an X-ray source at a desired position and then imaging an object by scanning it with a beam emanating from the X-ray source, which is received by the detector of a line scan camera, in which method the scanning motion is effected in such a way that the focal spot remains essentially stationary during the imaging process.

The inventive apparatus for implementing single-point projection imaging comprises an X-ray source and a line scan camera present at a set distance therefrom, the X-ray source as well as the line scan camera being adapted to rotate around an object to be placed therebetween, means for aligning the X-ray source's focal spot at a desired position, and means for effecting a scanning motion necessary for imaging the object in such a way that the focal spot remains essentially stationary during the imaging process. The alignment of the X-ray source's focal spot at a desired position is effected, e.g. by placing the object to be exposed between the X-ray source and the line scan camera by means of appropriate guides and supports at a set distance from the X-ray source's focal spot.

The apparatus comprises preferably a frame element, on which is mounted pivotably about a rotation axis an element housing an X-ray source and a line scan camera, said rotation axis being adapted for displacement relative to the frame element during a scanning motion, such that the centre of rotation is essentially in line with the focus, whereby the focus remains essentially stationary during a scanning motion. The rotation axis is preferably adapted for displacement along a linear path while the element housing the X-ray source and the line scan camera rotates to perform a scanning motion. Displacement of the rotation axis during a scanning motion can also be adapted to occur along a curving or meandering path, whereby a more accurate result is achieved regarding the immobility of the focus than by a combination of linear motion and rotary motion.

BRIEF DESCRIPTION OF THE DRAWINGS

The invention will now be described in more detail with reference to the accompanying drawings, in which.

DETAILED DESCRIPTION OF THE INVENTION

Figure 1:
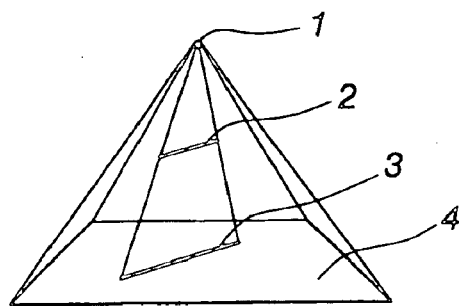
FIG. 1 shows the performance of prior art single-point projection imaging in a schematic view of principle.
Figure 2:
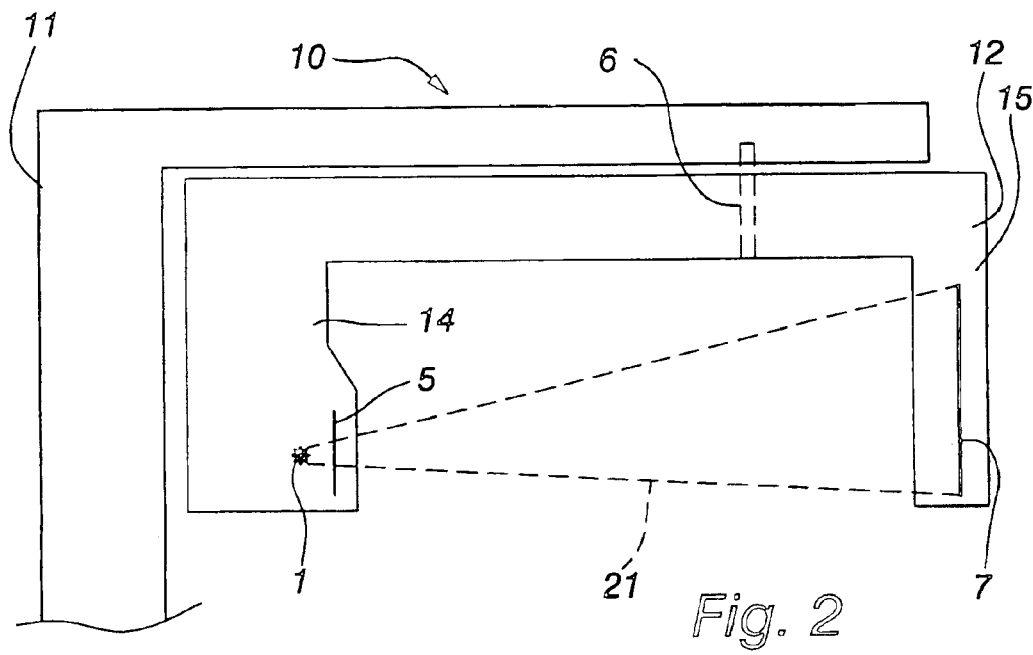
FIG. 2 shows one apparatus adaptable to a method of the invention in a schematic side view.

A panoramic X-ray apparatus 10 shown in FIG. 2 comprises a vertical member 11, from which extends a horizontal member 13 having suspended therefrom, pivotably about a rotation axis 6, a C-frame 12, having one 14 of its upright arms provided with an X-ray source with its focus indicated by reference numeral 1 and having a primary collimator in the vicinity thereof, indicated by reference numeral 6. A second upright arm 15 is provided with a line scan camera, including a detector 7, preferably a CCD detector.

The panoramic imaging apparatus and its operation is known as such for a skilled person. In panoramic imaging, an object to be imaged is placed between the arm members of the C-frame 12 by means of appropriate guides and supports, whereafter the X-ray source is activated and the C-frame 12 is rotated around the rotation axis 6, the primary collimator 5 having its aperture chosen in such a way that a beam 7 in a substantially vertical plane is focused on the detector 7, which is fitted behind the substantially vertical slit of a line scan camera mounted on the arm member 15 of the C-frame 12 and from which visual information is conveyed further, e.g. to a microprocessor. The operation of a line scan camera is described e.g. in U.S. patent Application 20030161438 A1 and the operation of a detector e.g. in U.S. Pat. No. 5,528,645, and, thus, those are not described in further detail in this specification.

Figure 3:
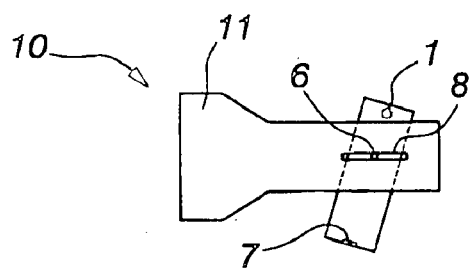
FIG. 3 shows the apparatus of FIG. 2 in a plan view.

According to FIG. 3, the rotation axis 6 is adapted for displacement in a slot 8 along a linear path.

Figure 4:
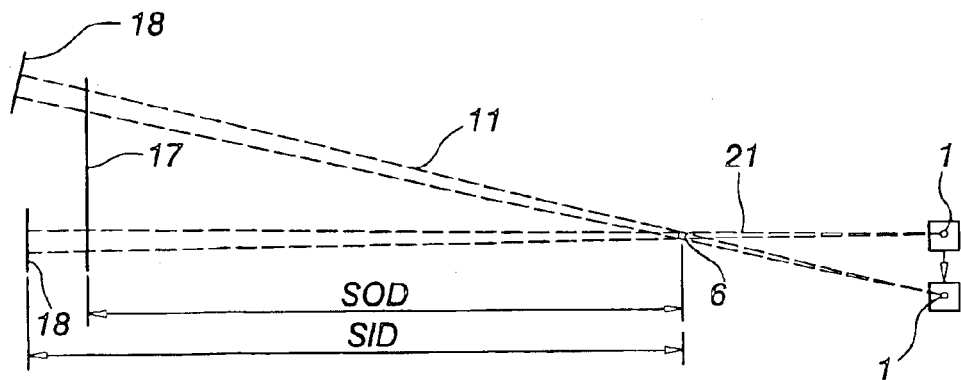
FIG. 4 shows schematically the impact on an effective focus created by a rotary motion of the X-ray source and the detector.

If imaging is performed by pivoting the X-ray source about the rotation axis 6 for imaging an object by means of a vertically directed beam 21, the vertical ratio of magnification remains the same as without a scanning motion but, on the other hand, the horizontal ratio of magnification changes, because the centre of rotation coinciding with the rotation axis 6 becomes an effective focal spot instead of the X-ray source's focal spot 1. FIG. 4 illustrates a situation, in which the rotation axis 6 remains stationary, whereby, as the X-ray source is rotating around a centre of rotation defined by the rotation axis 6, the X-ray beams 21 travel at each angular position through the centre of rotation, whereby the effective focal spot for radiation arriving at an image plane (detector) 18 by way of an object 17 will be constituted by the centre of rotation. The focus 1 moves relative to the object 17 during the rotary motion. Thus, the horizontal ratio of magnification, which is defined by the ratio of a distance between the focus and the image path (SID=source-Image distance) to a distance between the focus and the object (SOD=source-object distance), is equal to the ratio of a distance between a centre of rotation defined by the rotation axis 6 and the imaging plane 17 to a distance between the centre of rotation and the image path 18.

Figure 5:
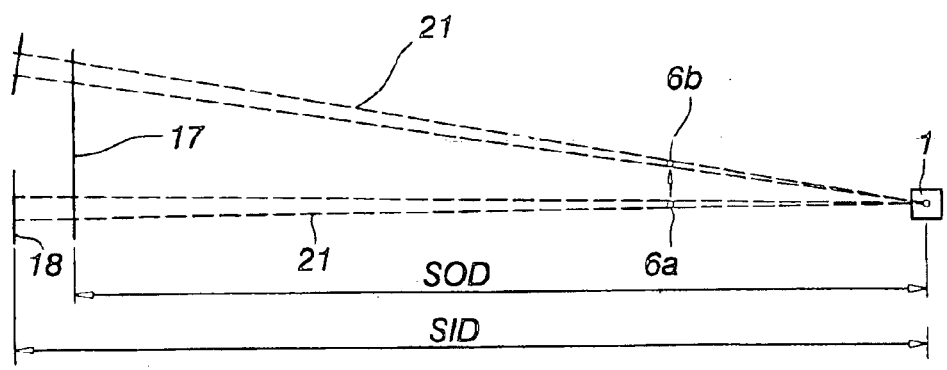
FIG. 5 shows schematically the position of an effective focus in the process of displacing the rotation axis during a rotary motion.

According to the invention, the rotation axis 6 is adapted for displacement preferably by a linear movement transversely to the beam 21. FIG. 5 illustrates a situation, in which the rotation axis has been displaced during a rotary motion by a linear movement from a position 6a to a position 6b, whereby the centre of rotation and hence the effective focal spot shifts to essentially coincide with the X-ray source's focus 1, said focus 1 remaining substantially stationary during the imaging process. In this case, both horizontal and vertical magnification is equal at each point between focus and detector and, hence, the ratio of magnification (SID/SOD) will be equal because the focus remains effectively stationary.

The inventive solution enables the use of presently available panoramic equipment for single-point projection imaging by providing the same with necessary programming modifications, which allow the execution of a scanning motion in such a way that the focus 1 remains essentially stationary during the imaging process unlike in panoramic tomography, in which the objective is to provide a slice image by means of a continuous steady movement of the effective focus.

What is claimed is:

1. A method for performing single-point projection imaging by using an X-ray apparatus, comprising an X-ray source and a line scan camera present at a set distance therefrom and provided with a digital detector, the X-ray source as well as the line scan camera being adapted to rotate around an object to be placed between the X-ray source and the line scan camera, said method comprising performing the alignment of the X-ray source's focal spot at a desired position and then imaging the object by scanning it with a beam emanating from the X-ray source, which beam is received by the detector of the line scan camera, in which method the scanning motion is effected in such a way that the focal spot remains essentially stationary during the imaging process.

2. A method as set forth in claim 1, the apparatus used therein comprising preferably a frame element, on which is mounted pivotably about a rotation axis an element housing an X-ray source and a line camera, said rotation axis being adapted for displacement relative to the frame element, such that, during implementation of the method, the centre of rotation is essentially in line with the focal spot, whereby the focus remains essentially stationary during a scanning motion.

3. An apparatus for performing single-point projection imaging, said apparatus comprising an X-ray source and a line scan camera present at a set distance therefrom, the X-ray source as well as the line scan camera being adapted to rotate during an imaging process around an object to be placed therebetween, said apparatus including means for aligning the X-ray source's focal spot at a desired position and means for effecting a scanning motion necessary for imaging the object in such a way that the focal spot remains essentially stationary during the imaging process.

4. An apparatus as set forth in claim 3, which comprises a frame element, on which is mounted pivotably about a rotation axis an element housing an X-ray source and a line scan camera, said rotation axis being adapted for displacement relative to the frame element during a scanning motion, such that the centre of rotation is essentially in line with the focal spot, whereby the focus remains essentially stationary during a scanning motion.

5. An apparatus as set forth in claim 4, wherein the rotation axis is adapted for displacement along a linear path while the element housing the X-ray source and the line scan camera rotates to perform a scanning motion.

* * * * *